United States Patent [19]
Lindstrom et al.

[11] Patent Number: 5,104,787
[45] Date of Patent: Apr. 14, 1992

[54] METHOD FOR APPARATUS FOR A DEFINED SERUMFREE MEDICAL SOLUTION USEFUL FOR CORNEAL PRESERVATION

[76] Inventors: Richard L. Lindstrom, 1065 W. Ferndale Rd., Wayzata, Minn. 55391; Debra Skelnik, P.O. Box 1758, Rte. 3, Cambridge, Minn. 55008

[21] Appl. No.: 487,919

[22] Filed: Mar. 5, 1990

[51] Int. Cl.$^5$ ............................................. A01N 1/02
[52] U.S. Cl. .................................... 435/1; 435/240.3; 435/240.2
[58] Field of Search ............................... 424/78; 435/1

[56] References Cited

U.S. PATENT DOCUMENTS 4,695,536 9/1987 Findstrom et al. ..................... 435/1

FOREIGN PATENT DOCUMENTS 648187 2/1979 U.S.S.R. ................................. 435/1

OTHER PUBLICATIONS

Foss, et al. Opthalmology, May 1989, vol. 96, No. 5, pp. 688–696.
Finstrom et al. Tr. Am. Ophth. Jor. vol. LXXXV, 1987.
K. Green et al. Invest Opthalmol. Vis. Sci. Nov. 78, pp. 1117–1120.
M. Taylor et al. Current Eye Research vol. 4, No. 9, 1985, pp. 963–973.

Primary Examiner—Thurman K. Page
Assistant Examiner—Peter Kulkosky
Attorney, Agent, or Firm—Hugh D. Jaeger

[57] ABSTRACT

A defined serumfree medical solution for applications in Ophthalmology, that contains one or more cell nutrient supplements which maintains and enhances the preservation of eye tissues, including human corneal tissues at low temperatures (2° C. to 15° C.). This solution is composed of a defined aqueous nutrient and electrolyte solution, supplemented with a glycosaminoglycan(s), a deturgescent agent(s), an energy source(s), a buffer system(s), an antioxidant(s), membrane stabilizing components, antibiotic(s), ATP precursors and nutrient cell supplements.

3 Claims, 4 Drawing Sheets

| Time After Keratoplasty | Defined Serumfree Medical Solution | Dexsol | Between-group |
|---|---|---|---|
| | Formula A | | |
| | Corneal Thickness mm | Corneal Thickness mm | P Value |
| Intraoperative | .623 ± .054 | .787 ± .047 | .002* |
| 1 Day | .708 ± .084 | | |
| 1 Week | .650 ± .084 | .743 ± .093 | .036* |

*Significant difference

METHOD FOR APPARATUS FOR A DEFINED SERUMFREE MEDICAL SOLUTION USEFUL FOR CORNEAL PRESERVATION

BACKGROUND OF THE INVENTION

1. Field of the Invention:

The present invention relates to the preservation of eye tissue in a defined nutritive, aqueous medical solution, and more particularly, relates to the preservation and enhancement of human corneal tissue, specified as the time between removal from the donor and transplantation.

2. Description of the Prior Art:

Keratoplasty, or transplantation of the cornea, has been effective in providing visual rehabilitation to many who suffer from corneal disorders. This procedure has gained widespread acceptance but has been severely hampered by the universally inconsistent availability of donor tissue. This problem made the development of a storage solution imperative. The development of MK TM -preservation medium, and subsequent chondroitin sulfate-containing media, has positively impacted the availability of quality donor tissue. Much research in this area has been undertaken with a view towards prolonging donor storage time and yet maintaining a viable endothelium, which is crucial to successful transplantation. Storage of the cornea for up to 14 days at 4° C. has been reported, although the current technology does not permit adequate tissue preservation beyond a few days. Storage longer than 96 hours is attended by epithelial decomposition and loss of corneal clarity, as demonstrated by increased swelling of the corneal stroma. This stromal edema is attributed to the decreased maintenance of the barrier pump function of the corneal endothelium, a specific cell layer lining the corneal stroma.

The functional status of the endothelium and sustained corneal deturgescence after corneal preservation are of great clinical importance, and contribute primarily to the success of the surgical outcome. The ability of the cornea to maintain a relatively dehydrated state is essential to the maintenance of corneal transparency. Corneal deturgescence is an energy-dependent phenomenon performed primarily by the endothelial cells. In order for the cornea to remain viable, various enzymatic reactions must occur to carry out energy-dependent functions, maintained by high levels of ATP.

The lower temperature of the 4° C. corneal storage method reduces the metabolic rate of the cornea, but the storage medium must still be able to support the basal requirements of the cornea. Thus, corneal storage media are a complex mixture of balanced salts, amino acids, energy sources, antioxidants, buffering agents, cell membrane stabilizers, glycosaminoglycans, deturgescents and antibiotics. Temperature reduction changes the membrane lipids, proteins and water structures, each of which could alter the active transport mechanism by hindering the ease of passive diffusion, carrier-substrate interaction and energy-coupling relationships. Thus disturbances of membrane function, as well as morphological and biochemical alterations, assume a greater consequence as the direct result of the lower metabolic rate. Therefore, a critical evaluation of physiologic parameters such as ionic and amino acid composition, bicarbonate equilibrium, available energy sources, dissolved oxygen levels, osmolality and pH should be observed with respect to each preservation medium. Parameters for extended 4° C. storage should be defined as to the reversibility of cell damage incurred during storage.

Adult corneal endothelium have a limited regenerative capacity and mitotic figures have been rarely observed in vivo; human corneal endothelium in vivo normally responds to trauma by sliding into the wounded area by cell migration. However, in vivo endothelial cell mitosis has been demonstrated in rabbits, cats and primates. In tissue culture, mitosis has been observed in rabbits and human corneal endothelium. Autoradiographic thymidine uptake studies after cryowounding or mechanical wounding of corneas in vitro has demonstrated existence of mitotic figures in the endothelial monolayer. Surgical trauma and disease can accelerate the loss of endothelial cells and further compromise the cornea. Thus, the long term preservation and enhancement of the corneal endothelium is a very important aspect of eye bank storage of eye tissue.

An overview of the issues surrounding the storage and handling of corneal tissue is found in Corneal Surgery, Chapters 1-4, pages 1-128 edited by Federick S. Brightbill, M.D., published by C. V. Mosby Company, St. Louis, MO, 1986. A variety of storage media and techniques have been proposed, and current research continues to be directed towards maintaining and actually enhancing the quality of donor tissues, and increasing the duration of storage corneal tissues, as defined as the time between excision from a donor and transplantation.

Accordingly, the present invention is directed toward materials and methods for enhancing ocular tissues, especially corneal tissues, during storage prior to transplantation. One aspect of the invention provides for the enhancement of corneal tissue viability by maintaining normal physiologic metabolism and corneal deturgescence during low temperature storage. Another aspect of the invention provides for increasing the length of time that eye tissues, especially corneal tissues, can maintain the attributes of fresh tissue.

SUMMARY OF THE INVENTION

Intermediate-term corneal storage at 4° C. should provide tissue preservation which is capable of sustaining the functional status of the endothelium. Experimental work has demonstrated that both human and animal eye tissues, especially corneas, are protected from deterioration and actually are enhanced during low temperature eye bank storage in a defined serum-free, nutrient supplemented preservation solution. The undesirable attributes of storage in serum-containing solutions are avoided, and the potential of the corneal endothelial cells to maintain normal physiologic metabolism and corneal deturgescence during low temperature storage is increased.

The corneal endothelium is responsible for preservation of the transparency of all corneal layers. The endothelium regulates the ion composition of the various corneal layers, thereby maintaining osmotic pressure, permitting permanent hydration of the cornea, and thus constant thickness and transparency. Consequently, any disturbance of endothelial cell function provokes corneal edema followed by partial or complete loss of transparency. The composition of synthetic media must address the increased stromal hydration that occurs with increased preservation time and reduced temperatures.

The remarkable capacity of the corneal stroma to uptake water is due to the presence of glycosaminoglycans (GAGS), such as chondroitin sulfate, dermatan or keratan sulfate between the collagen fibers. Electron microscopic studies comparing the collagen fibrils in swollen corneal stromas demonstrated that the diameter of collagen fibrils did not differ significantly from that of the normal fibrils. This finding suggests that it is, rather, the volume increase of the interfibrillar substance which is responsible for the swelling of the stroma. Additional refraction studies demonstrated that the hydration of the fibrils is unchanged despite the fact the cornea can swell from a state of near dryness to three times its normal thickness. When corneas are treated with hyaluronidase or cetylpyridinium chloride the stromal swelling is greatly reduced. These studies also suggest that the swelling takes place in the interfibrillar substances.

Glycosaminoglycans, such as chondroitin sulfate, are long, unbranched polysaccharide chains composed of repeating disaccharide units. Glycosaminoglycans are highly negatively-charged due to the presence of sulfate or carboxyl groups, or both, on many of the sugar residues. Glycosaminoglycan chains tend to adopt highly extended, random coiled conformations, and to occupy a huge volume for their mass. Being hydrophilic, they attract large amounts of water, thereby forming hydrated gels at even low concentrations. This tendency is markedly enhanced by their high density of negative charges, which attract osmotically active cations. This water-attracting property of glycosaminoglycans creates a swelling pressure, or turgor, in the extracellular matrix that resists compressive forces, in contrast to collagen fibrils, which resist stretching forces. Because of their porous and hydrated organization, the glycosaminoglycan chains allow the rapid diffusion of water soluble molecules.

Recent studies suggest that not only has the proteoglycan ground substance as a whole been implicated as playing a significant role in corneal hydration, but that the specific distribution of the different proteoglycans, which have different hydrating power, may also play a role in the establishment of water gradients across the cornea. The distribution of keratan sulfate and chondroitin-4-sulfate across the cornea directly relates to the asymmetric hydration of the cornea. There is greater chondroitin-4-sulfate concentration near the epithelium than near the endothelium; keratan sulfate is more concentrated near the endothelium. Keratan sulfate and predominantly keratan sulfate-bearing proteoglycans have great water sorptive capacity, but meager water retentive capacity. It is therefore plausible that the keratan sulfate-bearing proteoglycan gradient, highest at the endothelium, helps to set up the total water content gradient because of its great sorptive capacity. In contrast, the chondroitin-4-sulfate and dermatan sulfate-bearing proteoglycans, with their great water retentive capacity, can help establish the bound water gradient that is maximum near the epithelium. This gradient would then serve to diminish the dehydration of the front of the cornea, which is exposed to the atmosphere. Therefore, the water gradient across the cornea is highly correlative with the distribution of proteoglycans and their water sorptive and retentive capacities.

The present invention reduces intraoperative and postoperative rebound swelling associated with the use of chondroitin sulfate-containing preservation solutions. The increase of corneal swelling may be due to the influx of low molecular weight moieties of chondroitin sulfate into the stroma during prolonged low temperature storage. Additional fluid is imbibed through the cut edge of the scleral-corneal rim. The use of deturgescent agents, such as dextran and increased concentrations of chondroitin sulfate, control corneal hydration during low temperature storage. Dextran, a neutrally-charged molecule, osmotically restricts excess water from swelling the cornea during storage while chondroitin sulfate, a negatively charged molecule, actually binds to the cell membrane and provides a membrane stabilizing effect. Chondroitin sulfate and dextran assist in the prevention of stromal hydration by increasing the colloidal osmotic pressure in the aqueous environment surrounding the stored cornea. Sustained corneal deturgescence during and after corneal preservation are of great clinical importance, reducing handling and suturing problems encountered by the transplant surgeon, and consequently reducing the risk of graft failure.

The functional status of the endothelium and sustained corneal deturgescence after corneal preservation are of great clinical importance, and contribute primarily to the success of the surgical outcome. Other areas addressed in the present invention include the enhancement of corneal wound healing, and the reduction or elimination of the normal progressive loss of endothelial cells, through the use of nutritive cell supplements. Timely and adequate healing of corneal tissues is required to restore visual acuity.

There is a loss of corneal endothelial cells throughout life. In addition, endothelial cells are frequently damaged or destroyed in operations involving the anterior chamber. Damage by trauma or loss through aging is compensated by growth in size of the endothelial cells, which migrate to cover denuded surfaces of Descemet's membrane. In clinical cases, endothelial dysfunction is associated with variations of cell size rather than cell density. The appearance of increased numbers of giant cells contributes greatly to increased corneal edema. The junctions of giant cells are abnormal. These abnormalities in cell junctions increase the permeability of the intercellular spaces, thus increasing the fluid diffusion toward the cornea. The decreased density of organelles, such as mitochondria or rough endoplasmic reticulum, are diminished in giant cells. These organelles are essential for the adequate functions of the biological pump. Insufficient pump function results in excess accumulation of fluid in the corneal stroma. Furthermore, these giant cells have extended external membranes, supporting functional changes associated with decreased biological pump sites, associated with increased corneal swelling. It should be noted that disturbances in endothelial cell function leading to corneal edema occur when endothelial cell density falls to 40% of the normal value, when hexagonality falls to 33%, when the coefficient of variation of endothelial cell density increases three-to-four fold, and the size of giant cells has increased by 7.5 times over normal endothelial cells.

It is evident from these studies that the anterior chamber environment limits cell regeneration of the endothelium, and supports wound healing via cell migration. Extreme cell loss is compensated by the formation of giant cells. Furthermore, it is the complex interaction of the human corneal endothelial cell and the extracellular matrix that signal the cell to respond to cell loss in this manner.

The present invention further defines a nutritive solution that provides the cornea with additional amino acids, vitamins, trace minerals, and energy promoting precursors to enhance cell metabolism, wound healing and viability. Cell proliferation is regulated by events leading to DNA synthesis; whether or not a cell proceeds with DNA synthesis or is arrested in the early stages of the cell cycle is dependent upon extracellular conditions. Cellular metabolism can be enhanced by the addition of essential nutritive components by increasing hexose transport, glycogen transport, protein synthesis, amino acid and ion transport.

The novel defined nutrient containing solutions are serumfree. While serum-supplemented solution can stimulate limited mitosis in human corneal endothelial cells in tissue culture, the presence of serum in products for use with tissues for human transplantation presents many disadvantages. Serum can be an agent for the transmission of diseases, such as viral diseases. Non-human-derived sera contains many substances capable of eliciting an immune response, and all sera contain some substances such as endotoxins, and growth factors, that actually retard cell mitosis. These disadvantages are avoided by the present, serum-free solution.

Cornea preservation solutions are well known. In general, those employed herein contain an aqueous nutrient and electrolyte solution, a glycosaminoglycan, a deturgescent agent(s), an energy source(s), a buffer system(s), an antioxidant(s), membrane stabilizing components, antibiotic(s), ATP precursors and nutrient cell supplements. Nutrient and electrolyte solutions are well defined in the art of tissue-culturing. Such solutions contain the essential nutrients and electrolytes at minimal concentrations necessary for cell maintenance and cell growth. The actual composition of the solutions may vary greatly. In general, they contain inorganic salts, such as calcium, magnesium, iron, sodium and potassium salts of carbonates, nitrates, phosphates, chloride and the like, essential and non-essential amino acids, vitamins and other essential nutrients.

Chemically defined basal nutrient media are commercially available, for example from Gibco Laboratories (3175 Stanley Road, Grand Island, N.Y. 14073) and Microbiological Associates (P.O. Box 127, Briggs Ford Road, Walkersville, M.d. 21793) under the names Eagle's Minimal Essential Medium (MEM) and TC199. Corneal storage solutions have been adapted from these nutrient media. The defined serumfree medical solution base of the present invention is composed of components found in both MEM and TC199 supplemented with ATP precursors, vitamins, amino acids and growth promoting supplements. The defined serumfree medical solution is compared with commercially available corneal storage medium CSM TM developed by R. L. Lindstrom, M.D. and Debra L. Skelnik, B.S., available from Chiron Ophthalmics, Inc. (Irvine, CA) and TC199 from Gibco Laboratories (Grand Island, NY) in Table I.

| | TC199 mg/L | CSM mg/L | Formula A mg/L | AMINO ACIDS | M-K mg/L | CSM mg/L | Formula A mg/L |
|---|---|---|---|---|---|---|---|
| INORGANIC SALTS | | | | | | | |
| CaCl2 (anhyd) | 140 | 200 | 200 | DL Alanine | 50 | | |
| Fe(NO3)3 9H2O | 0.72 | | 0.5 | L Alanine | | 8.9 | 8.9 |
| KCl | 400 | 400 | 400 | L Arginine HCl | 70 | 126 | 126 |
| KH2PO4 | 60 | | | L Asparagine H2O | | 15 | 15 |
| MgSO4 7H2O | 200 | 200 | 200 | DL Aspartic acid | 60 | | |
| NaCl | 8000 | 6800 | 6800 | L Aspartic Acid | | 13.3 | 13.3 |
| NaHCO3 | | 2200 | 2200 | L Cysteine HCl H2O | 0.11 | | |
| NaH2PO4 H2O | | 140 | 140 | L Cystine | 26 | 24 | 24 |
| Na2HPO4 7H2O | 90 | | | DL Glutamic acid H2O | 150 | | |
| | | | | L Glutamic acid | | 14.7 | 14.7 |
| OTHER COMPONENTS | | | | L Glutamine | 100 | 292 | 292 |
| Adenine Sulfate | 10 | | 10 | Glycine | 50 | 7.5 | 7.5 |
| Adenosinetriphosphate- | | | | L Histidine HCl H2O | 21.88 | 42 | 42 |
| (Disodium Salt) | 1 | | | L Hydroxyproline | 10 | | 10 |
| Adenylic Acid | 0.2 | | | DL Isoleucine | 40 | | |
| Cholesterol | 0.2 | | 0.2 | L Isoleucine | | 52 | 52 |
| Deoxyribose | 0.5 | | | DL Leucine | 120 | | |
| D-Glucose | 1000 | 1000 | 1000 | L Leucine | | 52 | 52 |
| Glutathione (reduced) | 0.05 | | | L Lysine HCl | 70 | 72.5 | 72.5 |
| Guanine HCl | 0.3 | | | DL Methionine | 30 | | |
| Hypoxanthine | 0.3 | | | L Methionine | | 15 | 15 |
| (or) Hypoxanthine-Na salt | 0.344 | | | DL Phenylalanine | 50 | | |
| Phenol Red | 20 | 10 | 10 | L Phenylalanine | | 32 | 32 |
| Ribose | 0.5 | | | L Proline | 40 | 11.5 | 11.5 |
| Sodium acetate | 50 | | | DL Serine | 50 | | |
| Sodium Pyruvate | | 110 | 110 | L Serine | | 10.5 | 10.5 |
| Thymine | 0.3 | | | DL Threonine | 60 | | |
| Tween 80 | 20 | | | L Threonine | | 48 | 48 |
| Uracil | 0.3 | | | DL Tryptophan | 20 | | |
| Xanthine | 0.3 | | | L Trytophan | | 10 | 10 |
| | | | | L Tyrosine | 40 | 36 | 36 |
| | | | | DL Valine | 50 | | |
| | | | | L Valine | | 46 | 46 |

| | | | | | M-K mg/L | CSM mg/L | Formula A mg/L |
|---|---|---|---|---|---|---|---|
| | | INORGANIC SALTS | VITAMINS | | | | |
| | | CaCl2 (anhyd) | Ascorbic acid | | | 0.05 | 0.05 |
| | | Fe(NO3)3 9H2O | Alpha Tocopherol Phosphate | | | 0.01 | 0.01 |

| | | | | |
|---|---|---|---|---|
| KCl | (Disodium salt) | | | |
| KH2PO4 | d-Biotin | 0.01 | | 0.01 |
| MgSO4 7H2O | Calciferol | 0.1 | | 0.1 |
| NaCl | D-Ca pantothenate | 0.01 | 1 | 1 |
| NaHCO3 | Choline Chloride | 0.5 | 1 | 1 |
| NaH2PO4 H2O | Folic acid | 0.01 | 1 | 1 |
| Na2HPO4 7H2O | I-Inositol | 0.05 | 2 | 2 |
| | Menadione | 0.01 | | |
| OTHER COMPONENTS | Niacin | 0.025 | | 0.025 |
| Adenine Sulfate | Niacinamide | 0.025 | | |
| Adenosinetriphosphate- | Nicotinamide | | 1 | 1 |
| (Disodium Salt) | Para-aminobenzoic acid | 0.05 | | 0.05 |
| Adenylic Acid | Pyridoxal HCl | 0.025 | 1 | 1 |
| Cholesterol | Pyridoxine HCl | 0.025 | | 0.25 |
| Deoxyribose | Riboflavin | 0.01 | 0.1 | 0.1 |
| D-Glucose | Thiamine HCl | 0.01 | 1 | 1 |
| Glutathione (reduced) | Vitamin A (acetate) | 0.014 | | |
| Guanine HCl | | | | |
| Hypoxanthine | Adenosine | | | 5 |
| (or) Hypoxanthine-Na salt | Inosine | | | 10 |
| Phenol Red | Vitamin B12 | | | 1.36 |
| Ribose | | | | |
| Sodium acetate | Additional Components | | | |
| Sodium Pyruvate | 2-mercaptoethanol | | .5 mM | .5 mM |
| Thymine | Chondroltin Sulfate % | | 1.35 | 2.5 |
| Tween 80 | Gentamycin μg/ml | | 100 | 100 |
| Uracil | Dextran % | | | 1 |
| Xanthine | | | | |

DESCRIPTION OF THE PREFERRED EMBODIMENTS

Preferred defined serumfree medical solutions for use in the composition and methods of this invention contain an aqueous electrolyte solution (e.g. Minimal Essential Medium and/or TC199), a glycosaminoglycan (e.g. standard or purified high or low molecular weight chondroitin sulfate (A, B or C isomers), dermatan sulfate, dermatin sulfate, heparin sulfate, heparan sulfate, keratin sulfate, keratan sulfate and/or hyaluronic acid in a range of 0.01 mg/ml to 100 mg/ml; a deturgescent agent (e.g. low or high molecular weight polysaccharide, such as dextran, dextran sulfate, polyvinyl pyrrolidone, polyethylene glycol, polyvinyl acetate, hydroxypropylmethyl cellulose, carboxypropylmethyl cellulose) in a range of 0.01 mg/ml to 100 mg/ml; an energy source and carbon source (e.g. glucose, pyruvate, sucrose, fructose, dextrose) in a range of 0.05 mM to 10 mM; a buffer system (e.g. a bicarbonate buffer system and hydroxyethylpiperizene ethanesulfonic acid, HEPES buffer) in a range of 0.1 mM to 100 mM; to maintain a physiologic pH (desirably between 6.8 and 7.6), an antioxidant (e.g. ascorbic acid, 2-mercaptoethanol, glutathione, alpha tocopherol), in a range of .001 mM to 10 mM; membrane stabilizing agents (e.g. vitamins A and B, retinoic and/or cofactors, ethanolamine, and phosphoethanolamine, selenium and transferrin), in a range of 0.01 mg/ml to 500 mg/ml; antibiotics and/or antimucotic agents (e.g. amphotericin-B, gentamycin sulfate, kanamycin sulfate, neomycin sulfate, nystatin, penicillin, tobramycin, streptomycin sulfate) in a range of 0.001 mM to 10 mM; and ATP precursors (e.g. adenosine, inosine, adenine) in a range of 0.001 mM to 10 mM; and nutrient cell supplements (e.g. cholesterol, L-hydroxyproline, d-biotin, calciferol, niacin, para-aminobenzoic acid, pyridoxine HCl, Vitamin B12, Fe(-NO3)3, non-essential amino acids) in a range of 0.001 mM to 10 mM.

The serumfree medical solution of this invention is composed of a defined aqueous nutrient and electrolyte solution, supplemented with a glycosaminoglycan(s), a deturgescent agent(s), an energy source(s), a buffer system(s), an antioxidant(s), membrane stabilizing components, antibiotic(s), ATP precursors and nutrient cell supplements in the amounts sufficient to enhance cell metabolism, cell viability, wound healing, and corneal deturgescence following low temperature eye bank storage. The excised corneas are aseptically transferred to containers of the corneal storage solution, which are then sealed. For storage and transport, these corneas are maintained at low temperature (e.g. 2° C. to 15° C. optimally at 4° C.) to minimize the risk of bacterial growth and to reduce corneal tissue metabolic damage. It has been found that even at these low temperatures, the endothelial cells can be maintained for periods up to 14 days. At the time of transplant-ation, normal corneal deturgescence is maintained intraoperatively and post-operatively. Endothelial cell function and metabolism is maintained, permitting permanent hydration of the cornea, and thus constant thickness and transparency postoperatively. In addition to providing a viable cornea for transplantation, wound healing is potentiated. Various modifications can be made to the present invention without departing from the apparent scope thereof. For instance, the serumfree solution can be used in any medical application, and is not strictly limited to ophthalmology. The invention is further illustrated by the following examples, which is not intended to be limiting.

BRIEF DESCRIPTION OF THE FIGURES

Table I: Formulation of TC-199, CSM ™ and a representative formulation of the defined serumfree medical solution.

MODE OF OPERATION

Example One

A Defined Serumfree Medical Solution

Intermediate-term corneal storage at 4° C. should provide tissue preservation capable of sustaining the functional status of the endothelium and the maintenance of corneal deturgescence post-keratoplasty. CSM TM and K-Sol TM have become the standard media of intermediate-storage at 4° C. As demonstrated in Kaufman H. E., Varnell E. D., Kaufman S. et al. K-Sol TM corneal preservation. *Am J Ophthalmol* 1985. 100:299–304; Bourne W.M., Endothelial cell survival on transplanted human corneas preserved at 4° C. in 2.5% chondroitin sulfate for one to 13 days. *Am J Ophthalmol* 1986; 102:382–6; Lindstrom R. L., Skelnik D. L., Mindrup E. A., et al: Corneal preservation at 4° C. with chondroitin sulfate containing medium. *Invest Ophthalmol Vis Sci (Suppl)* 1987; 28 (3): 167; Bhugra M. K., Sugar A., Meyer R., et al: Results of a paired trial of MK TM and K-Sol TM storage. *Invest Ophthalmol Vis Sci (Suppl)* 1988; 29: 112 and Lass J. H., Reinhart W. J., Bruner W. E., et al. Comparison of corneal storage in K-Sol TM and Chondroitin Sulfate Corneal Storage Medium in human corneal transplantation. *Ophthalmology* 1989; 96: 688–97.

Increased corneal thickening is associated with CSM TM -stored corneas, with greater rebound swelling apparent at the time of surgery. However, normal corneal thickness is achieved during the first post-operative month. The increase of corneal swelling may be due to the influx of low molecular weight moieties of chondroitin sulfate into the stroma during prolonged storage at 4° C. In an effort to reduce corneal swelling, studies were conducted to determine if the addition of dextran to a defined serumfree chondroitin sulfate-containing medium would minimize corneal hydration.

Dextran, an effective osmotic agent in MK TM medium, keeps the cornea thin and effectively maintains the barrier function of the corneal endothelium. Corneas stored in dextran-containing medium are inhibited from swelling because of the colloidal osmotic pressure of dextran. The dextran is present to osmotically restrict excess water from swelling the cornea during storage. Dextran can penetrate the corneal endothelium and enter the stroma. This entrance and egress of dextran occurs rapidly at 4° C., with the degree of penetration of dextran depending on the length of storage and the condition of the endothelium. Thus, dextran was an attractive agent to reduce the corneal swelling associated with low temperature storage with chondroitin sulfate containing medium.

The defined serumfree medical solution consisted of Eagle's Minimal Essential Medium (MEM) supplemented with Earle's salts, sodium bicarbonate, 25 mM HEPES, 0.1 mM non-essential amino acids, 1 mM sodium pyruvate, 2 mM L-glutamine, 0.5 mM 2-mercaptoethanol, 1.0% dextran, 2.5% chondroitin sulfate and 100 µg/ml gentamycin sulfate. The base medium was further supplemented with the following components: $Fe(NO_3)_3 \cdot 9H_2O$, adenine sulfate, cholesterol, L-hydroxyproline, ascorbic acid, alpha tocopherol phosphate, D-biotin, calciferol, niacin, paraminobenzoic acid, pyridoxine HCl, adenosine, inosine, and vitamin B12. These components were added to more completely define the basal medium and potentiate cell growth and cell function (See Table I).

In order to determine the safety and efficacy of this defined serumfree medical solution, a dose response curve of chondroitin sulfate concentration with human corneas stored for 12 days at 4° C. was conducted. Chondroitin sulfate concentrations consisted of 1.5%, 1.75%, 2.0% and 2.5%. Corneal thickness measurements were taken at 0, 1, 7 and 12 days storage at 4° C.

In addition, isolation techniques developed in our laboratory have enabled the establishment of primary and subsequent subcultures of human corneal endothelium that retain the attributes of native endothelium. In vitro conditions maintain these human corneal endothelial cells in a proliferative state, actively undergoing mitosis. A quantitative bioassay has been developed to determine the effects of various test medium in the stimulation or inhibition of DNA synthesis as measured by $[^3H]$-thymidine incorporation.

Next a prospective pilot clinical trial was conducted, evaluating corneal thickness and endothelial cell survival for corneas that had been stored in a defined serumfree medical solution (Formula A) and then transplanted into patients.

Materials and Methods

Chondroitin Sulfate Dose Response Curve With Human Corneas

Human donor globes were immersed in 1.0% providone iodine in normal saline for three minutes, followed by a one-minute immersion in normal saline. The globes were then rinsed with 12 cc of normal saline with a syringe fitted with a 18-gauge needle. Sixteen paired corneas from donors unsuitable for transplantation because of age or cause of death were removed at a certified eye bank an average of 12.0 hours after death, and placed in 20 ml of defined medical solution supplemented with 1.5%, 1.75%, 2.0%, and 2.5% chondroitin sulfate. Control media was commercial Dexsol TM (Chiron Ophthalmics, Inc., Irvine, CA). Supplemented media was warmed to room temperature before the corneas were placed into the media, and corneal thickness measurements were taken. Corneal thickness measurements were made using a Leitz upright microscope fitted with a micrometer. The micrometer dial indicator was attached to the microscope stand above the stage, with the set screw placement through the stage, directly under the foot of the dial indicator. The corneal thickness measurement involved focusing on the endothelium, setting the set screw to bring the dial to 'zero', raising the stage to bring the epithelium into focus, and recording the dial indicator reading. The cornea was then cooled to 4° C., and stored for 12 days. Corneas were removed from the storage medium and placed in 15 ml of MEM supplemented with 2 mM L-glutamine and 100 µg/ml gentamycin. Corneas were then warmed to 34° C. for 2 hours and central corneal thickness measurements were taken at 30, 60 and 120 post-warming. Corneal endothelium was evaluated by staining with 0.1% trypan blue and alizarin red S after final corneal thickness measurements were taken.

$[^3H]$-Thymidine Incorporation of Human Corneal Endothelial Cells

Fourteen medium components were tested as follows: $Fe(NO_3)_3$ $9H_2O$, adenine sulfate, cholesterol, L-hydroxyproline, ascorbic acid, alpha tocopherol phosphate, D-biotin, calciferol, niacin, para-aminobenzoic acid, pyridoxine HCl, adenosine, inosine, and vitamin B12. Components were added individually or in combination to a base medium consisting of Eagle's Minimal Essential Medium (MEM) supplemented with Earle's salts, 25 mM HEPES, sodium bicarbonate, 0.1 mM non-essential amino acids, 1 mM sodium pyruvate, 2 mM L-glutamine, 0.5 mM 2-mercaptoethanol, 2.5% chondroitin sulfate and 100 µg/ml gentamycin sulfate. Additional chondroitin sulfate concentrations of 1.75% and 2.0% were also tested. Control media consisted of commercially available Dexsol TM (Chiron Ophthalmics, Inc., Irvine, CA) and CSM TM supplemented with 10% fetal bovine serum. All test media samples were freshly made up and warmed to room temperature at the time of the experiment.

Quantitative Bioassay

The quantitative bioassay is based on the incorporation of [$^3$H]-thymidine into the DNA of human corneal endothelial cells incubated in serumfree and serum containing medium. Costar 96-well tissue culture plates were seeded with $3 \times 10^3$ in a final volume of 200 µl of designated medium. Fourth passage human corneal endothelial cells were maintained in a humidified incubator at 35.5° C. in a 95% air: 5% $CO_2$ atmosphere. After 24 hours of incubation in CSM TM, supplemented with 10% fetal bovine serum, to permit attachment, the medium was removed, and each well was rinsed once with serumfree Minimal Essential Medium with Earle's salts and 25 mM HEPES. The cells were then rinsed and incubated with the appropriate test solution. Human corneal endothelial cells were then incubated for an additional 72 hours in the presence of 1 microcurie/well of [$^3$H]-thymidine. Uptake was ended by the aspiration of the radioactive medium and rinsing the cells twice with serumfree Minimal Essential Medium. The human corneal cells were detached with 0.5% trypsin and prepared for liquid scintillation counting. The [$^3$H]-thymidine counts represent acid-insoluble counts. One-way analysis of variance and the Newman-Keuls multiple range test were used to evaluate statistical significance ($p < 0.05$).

Clinical Trial

Eye Bank Procedures

Human donor globes were immersed in 1.0% povidone iodine in normal saline for three minutes, followed by a one-minute immersion in normal saline. The globes were then rinsed with 12 cc of normal saline with a syringe fitted with a 18-gauge needle. Corneas from suitable donors were removed at the eye bank an average of 8.6 hours after death, and placed in a defined serumfree medical solution (Formula A). This solution was warmed to room temperature before the cornea was placed into the solution. The cornea was then cooled to 4° C., and stored for an average of 4.3 days (range 1-7 days).

Recipient Criteria

The following recipient diagnoses were considered for entry into the study: aphakic bullous keratopathy, Fuchs' dystrophy, pseudophakic bullous keratopathy, corneal scar, keratoconus and failed graft. The preoperative examination consisted of measurement of best corrected visual acuity, intraocular pressure, slit lamp and funduscopic examination. Informed consent was obtained from all participants in clinical trials consistent with the United States Department of Health and Human Services guidelines. This randomized clinical trial was performed with Institutional Review Board consent and monitoring.

Surgical Technique

Corneas were warmed to room temperature at the time of transplantation. The donor buttons were cut from the endothelial side with a corneal trephine press. Sodium hyaluronate (Healon) or sodium hyaluronate with chondroitin sulfate (Viscoat) was used in all cases. Operative and postoperative care was similar for all cases. Suturing techniques consisted of a combination of 12 interrupted 10-0 sutures with a running 11-0 nylon or mersilene suture. Gentamycin, Betamethasone and Ancef were injected subconjunctivally at the end of each procedure.

Postoperative Treatment

Postoperatively all patients received neomycin -or gentamycin drops four times daily during the first month. Topical steroids were administered as needed. Patients were evaluated during the first two months postoperatively for complications, rejection, corneal vascularization, infection, wound leak, dehiscence of wound, persistent epithelial defects, and overall corneal condition. Ultrasonic pachymetry of the central cornea was performed preoperatively and postoperatively at one day, one week, one month and two months. The total number of patients included in this study was 15. Between group differences in corneal thickness were analyzed to determine if there were significant differences using a paired t-test.

Results and Discussion

Dextran Dose Response Curve With Human Corneas

Figure 1:
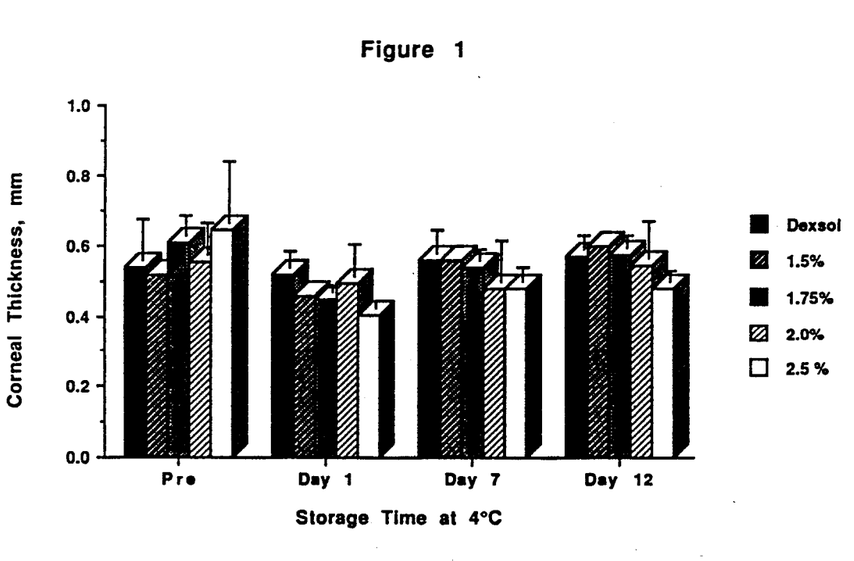
FIG. 1: Corneal Thickness of Human Corneas After 4° C. Storage.
Figure 2:
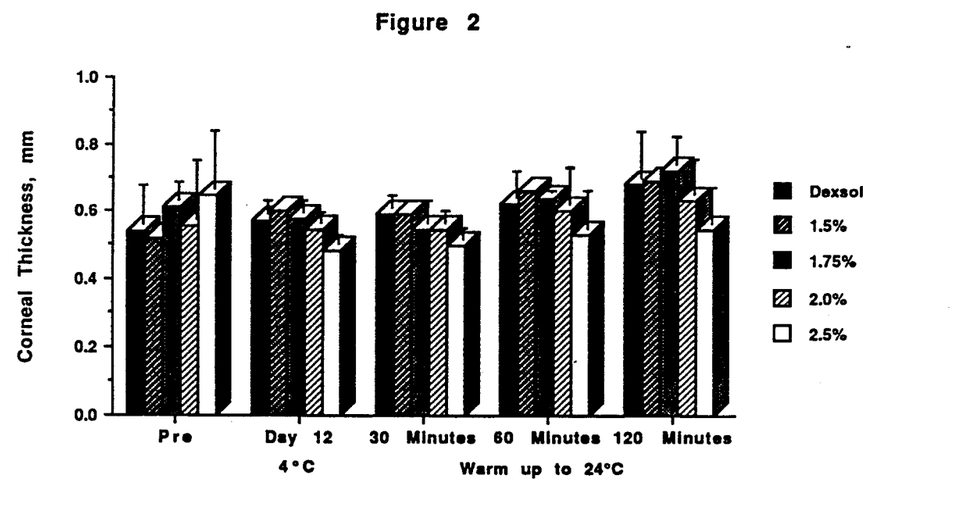
FIG. 2: Corneal Thickness After 12 Days Storage at 4° C. and Post Storage Warming to 24° C.

The chondroitin sulfate dose response curve for human corneas incubated at 4° C. for 12 days with respect to corneal thickness is shown in FIG. 1. Corneas incubated with Dexsol TM, containing 1.35% chondroitin sulfate, demonstrated effective thinning at 1, 7, and 12 days. Corneal thickness measurements at these time periods were $0.425 \pm 0.082$ mm, $0.53 \pm 0.04$ mm and $0.572 \pm 0.043$ mm. Corneas incubated with 1.5%-2.0% chondroitin sulfate demonstrated increased corneal deturgescence at these same time periods with the greatest corneal thinning occurring at 2.5% chondroitin sulfate. Corneal thickness at 1, 7, and 12 days post-incubation was $0.405 \pm 0.021$ mm, $0.48 \pm 0.042$ mm, $0.48 \pm 0.028$ mm, respectively. Corneas stored in Dexsol TM for 12 days exhibited a 19.6% increase in corneal swelling post warming to 34° C. Corneas stored in 1.5%-1.75% chondroitin sulfate demonstrated a statistically similar increase in corneal swelling post-warming. Corneas stored in 2.0% and 2.5% chondroitin sulfate demonstrated a 15.6% and 13.5% increase in corneal swelling post-warming (FIG. 2).

All endothelial cell monolayers were intact, with normal endothelial cell morphology for all concentrations of chondroitin sulfate tested. Corneas incubated with higher concentrations of chondroitin sulfate demonstrated fewer stromal folds, and fewer areas of alizarin red S staining of Descemet's membrane. All alizarin red S staining was minimal for all corneas, and was confined to areas of stromal folding. In conclusion, all corneas stored in 1.35%-2.5% chondroitin sulfate had intact corneal endothelium after 12 days preservation at 4° C. Corneas stored in the defined medical solution (containing 2.5% chondroitin sulfate) maintained the greatest corneal deturgescence over the 12 day preservation period. Minimal corneal folding and swelling was also noted for this test group after rewarming to 34° C. These results support the use of this defined serum-free medical solution to preserve human corneas at 4° C. for transplantation.

[³H]-Thymidine Incorporation of Human Corneal Endothelial Cells

Figure 3:
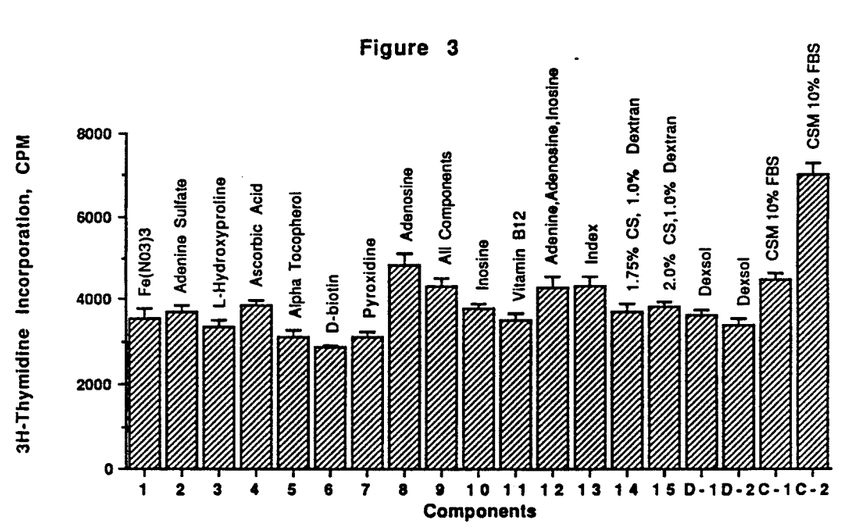
FIG. 3: [³H]-Thymidine Incorporation of Human Corneal Endothelial Cells Incubated With Defined Serumfree Medical Solution Components.

This study was conducted to evaluate the components of a defined serumfree medical solution. The test medium was evaluated in a [³H]-thymidine incorporation bioassay with human corneal endothelial cells. This bioassay provides a sensitive method to determine if the test medium will inhibit or stimulate the incorporation of [³H]-thymidine into the DNA of these cells. The incorporation of [³H]-thymidine by human corneal endothelial cells incubated with test medium containing one or more of fourteen components was compared to serumfree Dexsol TM medium and CSM TM medium supplemented with 10% FBS (FIG. 3). One-way analysis of variance and the Newman-Keuls multiple range test were used to evaluate statistical significance ($p < 0.05$).

In this bioassay, the cells were kept in a proliferative state, actively undergoing mitosis. Inhibition of [³H]-thymidine incorporation into the DNA of human corneal endothelial cells is an indicator of decreased cell metabolism, decreased cell health and possible cellular toxicity. Human corneal endothelial cells incubated with CSM TM medium supplemented with 10% FBS exhibited a statistically significant increase in [³H]-thymidine incorporation rate as compared to the freshly prepared control serumfree Dexsol TM medium. HCE cells incubated with 1.75% or 2.0% chondroitin sulfate exhibited statistically similar [³H]-thymidine incorporation rates as HCE cells incubated with serumfree Dexsol TM. The addition of 2.5% chondroitin sulfate and 1% dextran, in combination with the following individual components: $Fe(NO_3)_3 \cdot 9H_2O$, adenine sulfate, L-hydroxyproline, ascorbic acid, alpha tocopherol phosphate, D-biotin, pyridoxine HCl, inosine, and vitamin B12 exhibited statistically similar rates of [³H]-thymidine incorporation as HCE cells incubated with serumfree Dexsol TM. The addition of 2.5% chondroitin sulfate and 1% dextran, with adenosine or combination of adenosine, adenine, and inosine exhibited statistically greater [³H]-thymidine incorporation rates than HCE cells incubated with the Dexsol TM control medium. When all fourteen components were combined with 2.5% chondroitin sulfate in a supplemented MEM base, a statistically greater [³H]-thymidine incorporation rate was demonstrated as compared to the Dexsol TM control. All media tested maintained normal endothelial cell morphology throughout the 72-hour incubation period.

In conclusion, from the results of this [³H]-thymidine incorporation study with human corneal endothelial cells, a defined serumfree solution (Formula A) containing: 2.5% chondroitin sulfate, 1% dextran, $Fe(NO_3)_3 \cdot 9H_2O$, adenine sulfate, cholesterol, L-hydroxyproline, ascorbic acid, alpha tocopherol phosphate, D-biotin, calciferol, niacin, para-aminobenzoic acid, pyridoxine HCl, adenosine, inosine, and vitamin B12 was capable of stimulating [³H]-thymidine incorporation rates statistically greater than serumfree Dexsol TM medium as defined by the parameters of this bioassay. This defined serumfree medical solution is capable of enhancing the mitotic potential of human corneal endothelial cells, by providing a more completely defined solution than the Dexsol TM medium. This solution is therefore, acceptable for use as a 4° C. corneal preservation medium.

Clinical Study

Figure 4:
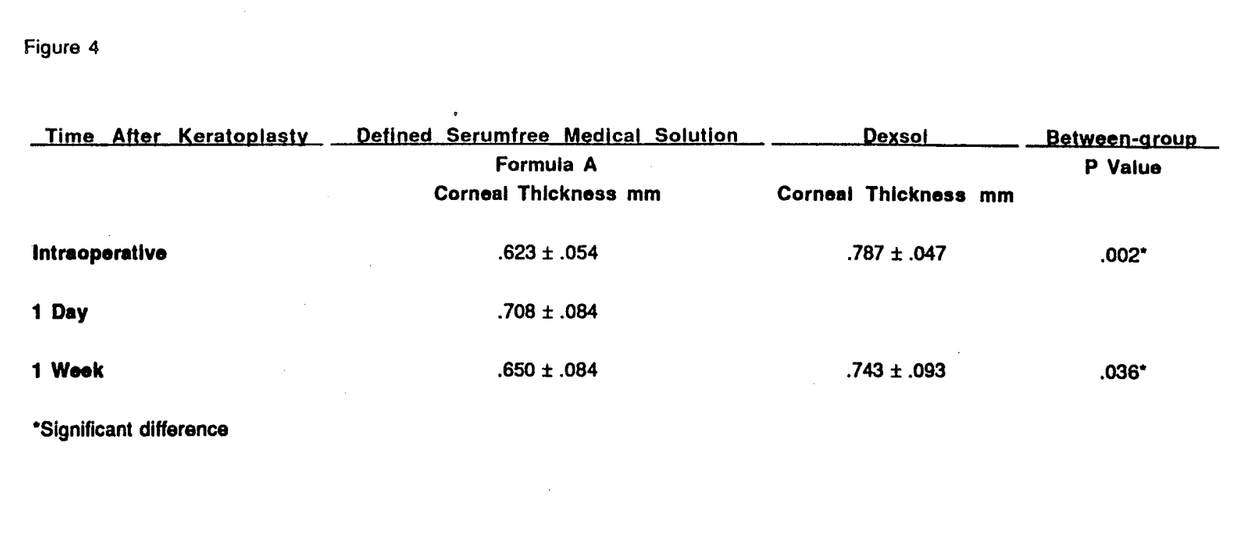
FIG. 4: Postoperative Corneal Thickness (mm).

Fifteen corneas were transplanted utilizing the defined serumfree medical solution (Formula A). All patients were operated on by one surgeon and were included in the following study. The cornea donors had the following characteristics: donor age (mean age $53 \pm 19$ years), death to enucleation time (mean: $4.3 \pm 2.7$ hours), and death to preservation time (mean: $4.3 \pm 3.2$ hours). Storage time of corneas at 4° C. was 4.3 days (range 1-7 days). One-hundred percent of the Formula A transplanted corneas were clear after 2 months. No persistent epithelial defects were noted in this patient group. Intraoperative corneal thickness was $0.623 \pm 0.054$ mm. Comparative corneal intraoperative thickness measurements of corneas stored in Dexsol TM under similar parameters was $0.787 \pm 0.047$ mm. Corneal thickness measurements at one week for Formula A and Dexsol stored corneas was $0.650 \pm 0.084$ mm and $0.743 \pm 0.093$ mm, respectively. Formula A stored corneas were significantly thinner intraoperatively and at one week post-operatively (FIG. 4). Progressive corneal thinning occurred for all patients during the 2 month follow-up period (corneal thickness: one month $0.612 \pm 0.167$ mm; two months $0.544 \pm 0.062$ mm). Postoperative intraocular pressures were within normal limits for all patients. No primary donor failures occurred in this Formula A cornea group.

The defined serumfree medical (Formula A) solution was effective in maintaining normal corneal deturgescence intraoperatively and postoperatively. Endothelial cell function and metabolism was maintained, permitting normal hydration of the cornea, and thus sustaining constant corneal thickness and transparency postoperatively.

We claim:

1. The defined serumfree medical solution consisting essentially of
   a. an aqueous nutrient and electrolyte solution selected from the group of:
      1. Eagle's minimal essential medium (MEM)
      2. TC199 medium
      3. A combination of Eagle's minimal essential medium (MEM) and TC199
   b. a glycosaminoglycan in the range of 0.01 mg/ml to 100 mg/ml selected from the group of:
      1. chondroitin sulfate;
      2. dermatan sulfate;
      3. dermatin sulfate;
      4. heparin sulfate;
      5. heparan sulfate;
      6. keratin sulfate;
      7. keratan sulfate; and/or
      8. hyaluronic acid,
   c. a deturgescent agent in the range of 0.01 mg/ml to 100 mg/ml selected from the group of:
      1. dextran;
      2. dextran sulfate;
      3. polyvinyl pyrrolidone;
      4. polyethylene glycol;
      5. polyvinyl acetate;
      5. hydroxypropylmethyl cellulose; and
      6. carboxypropylmethyl cellulose,
   d. an energy source in a range of 0.05 mM to 10 mM selected from the group of:
      1. glucose;
      2. pyruvate;
      3. sucrose;

4. fructose; and
5. dextrose,
e. a buffer system in a range of 0.1 mM to 100 mM selected from the group of:
1. Bicarbonate buffer; and
2. HEPES buffer,
f. an antioxidant in a range of 0.001 mM to 10 mM selected from the group of:
1. ascorbic acid;
2. 2-mercaptoethanol;
3. glutathione; and
4. alpha-tocopherol,
g. a membrane stabilizing component in a range of 0.01 mg/ml to 500 mg/ml selected from the group of:
1. vitamin A;
2. vitamin B;
3. retinoic acid;
4. ethanolamine;
5. phosphoethanolamine;
6. selenium; and
7. transferrin,
h. an antibiotic and/or antimycotic in the range of 0.1 μg/ml to 1 mg/ml selected from the group of:
1. amphotericin-B;
2. gentamycin sulfate;
3. kanamycin sulfate;
4. neomycin sulfate;
5. nystatin;
6. penicillin;
7. tobramycin; and
8. streptomycin,
i. ATP presursors in a range of 0.001 mM to 10 mM selected from the group of:
1. adenosine;
2. inosine; and
3. adenine,
j. Nutrient cell supplements in a range of 0.001 mM to 10 mM selected from the group of:
1. cholestrol;
2. L-hydroxyproline;
3. d-biotin;
4. calciferol;
5. niacin;
6. para-aminobenzoic acid;
7. pyridoxine HCl;
8. vitamin B12;
9. Fe(NO3)3; and
10. non-essential amino acids,
wherein said solution is effective in maintaining corneal deturgescence, thickness, and transparency intraoperatively and postoperatively 2. A defined serumfree medical solution containing components which maintain and enhance the preservation of eye tissues, including human corneal tissues at low temperatures (2° C. to 15° C.) with a physiological pH consisting essentially of
a. an aqueous nutrient and electrolyte solution:
1. Eagle's minimal essential medium (MEM)
b. a glycosaminoglycan
1. 2.5% chondroitin sulfate;
c. a deturgescent agent
1. 1% dextran;
d. an energy source
1. 110 mg/L pyruvate;
2. 1000 mg/L glucose
e. a buffer system
1. 2200 mg/L Bicarbonate buffer; and
2. 25 mM HEPES buffer,
f. an antioxidant
1. 0.5 mM 2-mercaptoethanol; and
2. 0.01 mg/L alpha-tocopherol,
g. an antibiotic and/or antimycotic
1. 100 mg/L gentamycin sulfate;
h. ATP presursors
1. 5 mg/L adenosine;
2. 10 mg/L inosine; and
3. 10 mg/L adenine,
i. Nutrient cell supplements
1. 0.2 mg/L cholestrol;
2. 10 mg/L L-hydroxyproline;
3. 0.01 mg/L d-biotin;
4. 0.1 mg/L calciferol;
5. 0.025 mg/L niacin;
6. 0.05 mg/L para-aminobenzoic acid;
7. 0.25 mg/L pyridoxine HCl;
8. 1.36 mg/L vitamin B12;
9. 0.5 mg/L Fe(NO3)3; and
10. 0.1 mM non-essential amino acids,
wherein said solution is effective in maintaining corneal deturgescence, thickness and transparency intraoperatively and postoperatively.

3. A method for the storage and preservation of corneas and/or corneal tissue, the method comprising bringing said tissue into contact with a solution according to calim 2.

* * * * *